(12) United States Patent
Shi et al.

(10) Patent No.: US 11,628,207 B2
(45) Date of Patent: Apr. 18, 2023

(54) USE OF THERMOLYSIN TO REDUCE OR ELIMINATE BACTERIAL BIOFILMS FROM SURFACES

(71) Applicant: SMITH & NEPHEW, INC., Memphis, TN (US)

(72) Inventors: Lei Shi, Memphis, TN (US); Catherine Van Der Kar, Memphis, TN (US); Aleksa Jovanovic, Memphis, TN (US); Eric Roche, Memphis, TN (US)

(73) Assignee: SMITH & NEPHEW, INC., Memphis, TN (US)

( * ) Notice: Subject to any disclaimer, the term of this patent is extended or adjusted under 35 U.S.C. 154(b) by 204 days.

(21) Appl. No.: 16/319,927

(22) PCT Filed: Jul. 26, 2017

(86) PCT No.: PCT/IB2017/054535
§ 371 (c)(1),
(2) Date: Jan. 23, 2019

(87) PCT Pub. No.: WO2018/020435
PCT Pub. Date: Feb. 1, 2018

(65) Prior Publication Data
US 2019/0262437 A1 Aug. 29, 2019

Related U.S. Application Data

(60) Provisional application No. 62/367,338, filed on Jul. 27, 2016.

(51) Int. Cl.
*A61K 38/48* (2006.01)
*A01N 25/34* (2006.01)
(Continued)

(52) U.S. Cl.
CPC .......... *A61K 38/4886* (2013.01); *A01N 25/34* (2013.01); *A01N 33/18* (2013.01);
(Continued)

(58) Field of Classification Search
None
See application file for complete search history.

(56) References Cited

U.S. PATENT DOCUMENTS

| 4,197,291 | A | 4/1980 | Klein et al. |
| 5,902,600 | A | 5/1999 | Woller et al. |

(Continued)

FOREIGN PATENT DOCUMENTS

| EP | 0590746 | 4/1994 | |
| EP | 590746 A1 * | 4/1994 | ............ C02F 3/342 |

(Continued)

OTHER PUBLICATIONS

Sugimoto et al., "*Staphylococcus epidermidis* Esp Degrades Specific Proteins Associated with *Staphylococcus aureus* Biofilm Formation and Host-Pathogen Interaction", Journal of Bacteriology, Jan. 2013, 195 (8), pp. 1645-1655. (Year: 2013).*

(Continued)

*Primary Examiner* — Carlos A Azpuru
*Assistant Examiner* — Casey S Hagopian
(74) *Attorney, Agent, or Firm* — Norton Rose Fulbright US LLP (57) ABSTRACT

Methods are disclosed for the reduction or elimination of bacterial biofilms on biological and non-biological surfaces, as well as methods for the treatment of wounds, skin lesions, mucous membrane lesions, and other biological surfaces infected or contaminated with bacterial biofilms using compositions comprising thermolysin.

15 Claims, 1 Drawing Sheet

(51) Int. Cl.

| | | |
|---|---|---|
| *A01N 33/18* | (2006.01) | |
| *A61L 29/16* | (2006.01) | |
| *A61L 31/16* | (2006.01) | |
| *A61L 27/54* | (2006.01) | |
| *A61L 27/34* | (2006.01) | |
| *A61L 31/10* | (2006.01) | |
| *A61L 29/08* | (2006.01) | |

(52) U.S. Cl.
CPC ............ *A61L 27/34* (2013.01); *A61L 27/54* (2013.01); *A61L 29/085* (2013.01); *A61L 29/16* (2013.01); *A61L 31/10* (2013.01); *A61L 31/16* (2013.01); *C12Y 304/24027* (2013.01); *A61L 2300/254* (2013.01)

(56) References Cited

U.S. PATENT DOCUMENTS

| | | |
|---|---|---|
| 6,172,219 B1 | 1/2001 | Callegaro et al. |
| 6,399,092 B1 | 6/2002 | Hobson et al. |
| 6,479,060 B1 | 11/2002 | Jones et al. |
| 6,548,566 B1 | 4/2003 | Hobson et al. |
| 7,294,497 B2 | 11/2007 | Kaplan |
| 7,459,155 B2 | 12/2008 | Margolin et al. |
| 7,642,079 B2 | 1/2010 | Caynouette et al. |
| 7,785,584 B2 | 8/2010 | Jones et al. |
| 8,066,991 B2 | 11/2011 | Jolly |
| 8,119,124 B2 | 2/2012 | Gorecki et al. |
| 8,383,101 B2 | 2/2013 | Olmstead |
| 8,632,769 B2 | 1/2014 | Barron |
| 8,680,072 B2 * | 3/2014 | Onsoyen ............ A61K 31/7036 536/3 |
| 8,809,031 B2 | 8/2014 | England et al. |
| 9,694,100 B2 | 7/2017 | Shi et al. |
| 10,058,596 B2 | 8/2018 | Hanson |
| 2003/0026794 A1 | 2/2003 | Fein |
| 2003/0027310 A1 | 2/2003 | Berka et al. |
| 2003/0198631 A1 | 10/2003 | Shi et al. |
| 2003/0198632 A1 | 10/2003 | Shi et al. |
| 2005/0079594 A1 * | 4/2005 | Marion ............... C11D 3/38627 435/196 |
| 2005/0158299 A1 | 7/2005 | Margolin et al. |
| 2007/0264715 A1 | 11/2007 | Robinson et al. |
| 2010/0124549 A1 | 5/2010 | Studin |
| 2010/0221237 A1 | 9/2010 | Kokai-Kun et al. |
| 2010/0254968 A1 | 10/2010 | Desser et al. |
| 2012/0258089 A1 | 10/2012 | Madhyastha et al. |
| 2013/0045196 A1 | 2/2013 | Shi et al. |
| 2014/0154235 A1 | 6/2014 | Shi et al. |
| 2015/0118219 A1 | 4/2015 | Shi et al. |
| 2015/0283217 A1 | 10/2015 | Shi et al. |
| 2016/0008293 A1 | 1/2016 | Shi et al. |
| 2018/0289003 A1 | 10/2018 | Jovanovic et al. |

FOREIGN PATENT DOCUMENTS

| | | |
|---|---|---|
| JP | S56-092217 | 7/1981 |
| JP | H06-262165 | 9/1994 |
| JP | 2008-290966 | 12/2008 |
| JP | 2010-126710 | 6/2010 |
| WO | WO 02/051436 | 7/2002 |
| WO | WO 2005/018695 | 3/2005 |
| WO | WO 2005/047514 | 5/2005 |
| WO | WO 2005/115357 | 12/2005 |
| WO | WO 2006/037606 | 4/2006 |
| WO | WO 2008/019417 | 2/2008 |
| WO | WO 2009/068841 | 6/2009 |
| WO | WO 2010/079209 | 7/2010 |
| WO | WO 2010/112848 | 10/2010 |
| WO | WO 2011/063394 | 5/2011 |
| WO | WO 2011/071986 | 6/2011 |
| WO | WO 2011/163237 | 12/2011 |
| WO | WO 2012/155027 | 11/2012 |
| WO | WO 2014/078581 | 5/2014 |
| WO | WO-2014078581 A1 * | 5/2014 ......... A61K 38/4886 |
| WO | WO 2014/145037 | 9/2014 |
| WO | WO2015/155351 | 10/2015 |

OTHER PUBLICATIONS

Attinger et al. "Clinically Addressing Biofilm in Chronic Wounds", Advances in Wound Care, vol. 1, No. 3, Jun. 2012, pp. 127-132. (Year: 2012).*

Foster, T. Chapter 12 *Staphylococcus*, Medical Microbiology, 4th Ed., Galveston (TX): University of Texas Medical Branch at Galveston; 1996. (Year: 1996).*

Scales et al. "Microbiology, genomics, and clinical significance of the Pseudomonas fluorescens species complex, an unappreciated colonizer of humans." Clinical microbiology reviews vol. 27,4 (2014): 927-48. (Year: 2014).*

Thomas et al. "A Lethal Case of Pseudomonas putida Bacteremia Due to Soft Tissue Infection." Infectious diseases in clinical practice (Baltimore, Md.) vol. 21,3 (2013): 147-213. (Year: 2013).*

Freney et al. "Postoperative infant septicemia caused by Pseudomonas luteola (CDC group Ve-1) and Pseudomonas oryzihabitans (CDC group Ve-2)."Journal of clinical microbiology vol. 26,6 (1988): 1241-3. (Year: 1988).*

O'Meara et al. "Antibiotics and antiseptics for venous leg ulcers", Cochrane Database of Systematic Reviews, Jan. 2014, Issue 1, Abstract only, pp. 1-4. (Year: 2014).*

Sigma Aldrich, "Thermolysin" product sheet, Accessed online on Mar. 19, 2021 at [https://www.sigmaaldrich.com]._Internet Archive_. [http://web.archive.org/web/20150629020349/https://www.sigmaaldrich.com/catalog/product/sigma/p1512?lang=en&region=US], (Year: 2015).*

"Research on Microbial Biofilms" National Institutes of Health, PA No. PA-03-047, 2002, Accessed from the Internet on Jan. 15, 2019, URL < https://grants.nih.gov/grants/guide/pa-files/pa-03-047.html >.

Ahn et al., "Robust trypsin coating on electrospun polymer nanofibers in rigorous conditions and its uses for protein digestion" *Biotechnol. Bioeng.*, 2010, 107:917-923.

Akiyama et al., "Recent Investigations of *Staphylococcus aureus* in Dermatology" *Japanese Journal of Dermatology*, 1999, 109(13):2095-2102. (English Translation).

Barbera et al., "Multicentre clinical study on seaprose S in acute and chronic respiratory inflammation" *Minuerva Cardioangiol*, 1996,35(4):49-156.

Bjarnsholt "Why chronic wounds will not heal: a novel hypothesis" *Wound Repair and Regeneration*, 2008, 16(1):2-10.

Borriello et al., "Oxygen Limitation Contributes to Antibiotic Tolerance of *Pseudomonas aeruginosa* in Biofilms" *Antimicrobial Agents and Chemotherapy*, 2004, 48(7):2659-2664.

Bracale and Selvetella, "Clinical study of the efficacy of and tolerance to seasprose S in inflammatory venous disease. Controlled study versus serration-peptidatse" *Minerva Cardioangiol*, 1996, 44(10):515-524.

Braga et al., "Effects of Seaprose on the Rheology of Bronchial Mucus in Patients with Chronic Bronchitis. A Double-Blind Study vs. Placebo" *Int. J. Clin. Pharm. Res.*, 1993, 8(3):179-185.

Braga et al., "In Vitro Rheological Assessment of Mucolytic Activity Induced by Seaprose" *Pharmacological Research*, 1990, 22(5):611-617.

Braga et al., "The influence of seaprose on erythromycin penetration into bronchial mucux in bronchopulmonary infections," *Drugs Exp. Clin. Res.*, 1992; 18(3):105-111 (Abstract Only).

Dindelli et al., "Clinical efficacy and safety of Seaprose S in the treatment of surgical wound complications in puerperium" *Minerva Cardioangiol.*, 1990, 42(7-8):313-315.

Drug Information Sheet; Teoase Tablets, 15mg, Revised Mar. 2008, 1 page.

Enzyme Handbook, Springer-Verlag Berlin Heidelber, 1998, pp. 1-8.

Falanga, Vincent "Wound Bed Preparation and the Role of Enzymes: A Case for Multiple Actions of Therapeutic Agents" *Wounds*, 2002, 14(2):47-50.

(56) References Cited

OTHER PUBLICATIONS

Fossati, "Antiinflammatory Effects of Seaprose-S on Various Inflammation Models" *Drugs Exptl. Clin. Res.*, 1999, 25(6):263-270.
International Preliminary Report on Patentability issued in PCT Application No. PCT/US2012/037480, dated Nov. 21, 2013.
International Search Report and Written Opinion issued in International Patent Application No. PCT/IB2017/054535, dated Oct. 27, 2017.
International Search Report and Written Opinion issued in PCT Application No. PCT?US2012/037480, dated Jul. 16, 2012.
Jacobsen "Investigating the humoral immune response in chronic venous leg ulcer patients colonised with *Pseudomonas aeruginosa*" *International Wound Journal*, 2011, 8(1):33-43.
James et al., "Biofilms in Chronic Wounds" *Wound Repair Regen*, 2008, 16:37-44.
Kiedrowski et al., "New approaches for treating staphylococcal biofilm infections" *Ann. N. Y. Acad. Sci.*, 2011, 1241:104-121.
Luisetti et al., "Some Properties of the Alkaline Proteinase From Aspergillus melleus" *Int. J. Tiss. Reac.*, 1991, 13(4):187-192.
Mertz, "Cutaneous Biofilms: Firend or Foe?" *Wounds*, 2003, 15:1-9.
Miyazaki et al., "The Effect of SA-001 (Jeoase) on the Pharyngolaryngeal Complications Following Endotracheal Anesthesia" *Masui (Anesthesia)*, 1969, 18(8):722-730.
Moretti et al., "Effects of Seaprose on Sputum Biochemical Components in Chronic Bronchitic Patients: A Double-Blind Study vs. Placebo" *Int. J. Clin. Phar. Res*, 1993, 8(5):275-280.
Morihara et al., "Comparative study of the various serine alkaline proteinases from microorganisms. Esterase activity against N-acylated peptide ester substrates" *Archives of Biochemistry and Biophysics*, 1974, 165:72-79.
Nakatani et al., "Interaction of Asp. melleus Semi-Alkaline protease with benzeneboronic acid" *J. Biochem.*, 1972, 81(5): 1269-1272.
Ogawa et al., "The evaluation of the effect of bromelain ointment of the debridement of eschar of burn, decubitus and various wound" *Journal of New Remedies & Clinics*, 1999, 48(10):1301-1309. (English Abstract).
Ohjimi, "Wounds and Infection—Clinical Conditions and Diagnosis of Wounds Infections and Therapeutic Strategies Therefore," *Plastic and Reconstructive Surgery Today*, 2010, 6:1-5.
Page, "Description of Skin Lesions" Merck Manual, 2016, Accessed from the Internet on Jan. 15, 2019, URL < https://www.merckmanuals.com/professional/dermatologic-disorders/approach-to-the-dermatologic-patient/description-of-skin-lesions >.
Polini et al., "Collagen-functionalised electrospun polymer fibers for bioengineering applications" *Soft Matter*, 2010, 6:1668-1674.

Sasaki, Database WPI, Tomson Scientific, XP-002678257, Dec. 4, 2008.
Shi et al., "Evaluation of Wound Debridement Efficacy of Proteolytic Enzymes From the Fungus Aspergillus melleus" *Wound Repair and Regeneration*, 2012, 20(2):A39. (Abstract Only).
Spadari et al., "Highly restricted specificity of the serine proteinase aspergillopeptidase B" *Biochimica et Biophysica Acta*, 1974, 359:267-272.
Sugimoto et al., "*Staphylococcus epidermidis* Esp Degrades Specific Proteins Associated with *Staphylococcus aureus* Biofilm Formation and Host-Pathogen Interaction" *Journal of Bacteriology*, 2013, 195(8):1645-1655.
Tiwari, "Burn Wound: How it Differs from Other Wounds?" *Indian Journal of Plastic Surgery*, 2012, 45(2):364-373.
Turkova et al., "Alkaline proteinases of the genus Aspergillus" *Biochimica et Biophysica Acta*, 1972, 257:257-263.
Van der Kar et al., "A Versatile In Vitro biofilm Model Using Two Wound Pathogens to Screen Formulations" *2010 Wound Healing Society Annual Meeting*, Poster BRC09, 2010.
Williamson et al., "Heterogeneity in *Pseudomonas aeruginosa* Biofilms Includes expression of Ribosome Hibernation Factors in the Antibiotic-Tolerant Subpopulation and Hypoxia-Induced Stress Response in the Metabolically Active Population" *Journal of Bacteriology*, 2012, 194(8): 2062-2073.
Zheng et al., "Penetration of Rifampin through *Staphylococcus epidermidis* Biofilms" *Antimicrobial Agents and Chemotherapy*, 2002, 46(3):900-903.
Benedetti, Julia, "Description of Skin Lesions" Merck Manual Professional Version, Feb. 2019, 12 pages.
Das et al., "Attenuation of Pseudomonas aeruginosa biofilm formation by Vitexin: A Combinatorial study with azithromycin and gentamicin," Scientific Reports, 2016, 6:23347, 13 pages.
Mingeot-Leclercq et al., "Aminoglycosides: Activity and Resistance," *Antimicrob. Agents. Chemother.*, 1999, 43(4):727-737.
Moro et al., "Atrial natriuretic peptide inhibits the production of adipokines and cytokines linked to inflammation and insulin resistance in human subcutaneous adipose tissue" *Diabetologia*, 2007, 50:1038-1047.
Banar et al., "Evaluation of mannosidase and trypsin enzymes effects on biofilm production of Pseudomonas aeruginosa isolated from burn wound infection", *PLoS One*, Oct. 2016, pp. 1-13.
Mu et al., "Potent Antibacterial Nanoparticles against Biofilm and Intracellular Bacteria" *Scientific Reports* 2016, 6:18877, 9 pages.
Zhao et al., "Biofilms and Inflammation in Chronic Wounds" *Advances in Wound Care* 2013, 2(7), 389-399.

* cited by examiner

USE OF THERMOLYSIN TO REDUCE OR ELIMINATE BACTERIAL BIOFILMS FROM SURFACES

CROSS-REFERENCE TO RELATED APPLICATIONS

This application is a national phase application under 35 U.S.C. § 371 of International Application No. PCT/IB2017/054535, filed Jul. 26, 2017, which claims benefit to U.S. Provisional Patent Application No. 62/367,338, filed Jul. 27, 2016. The entire contents of the referenced applications are incorporated herein by reference.

FIELD OF THE INVENTION

The present invention generally relates to methods and compositions useful for reducing or eliminating bacterial biofilms on surfaces. The compositions include thermolysin as an active ingredient to reduce or eliminate the bacterial biofilms.

BACKGROUND OF THE INVENTION

Bacterial biofilms are populations of bacteria attached to a surface. Bacteria in a biofilm are frequently embedded within a self-produced matrix of an extracellular polymeric substance (EPS), which holds the bacteria together in a mass and firmly attaches the bacterial mass to the underlying surface. The bacterial biofilm EPS, which is often referred to as slime, is a polymeric conglomeration generally composed of extracellular DNA, proteins, polysaccharides and various biopolymers. Biofilms can form on biological or non-biological surfaces and can be prevalent in both industrial and clinical settings.

Evidence has shown that biofilms constitute a significant threat to human health. Biofilms are responsible for more than 80% of microbial infections in the body ("Research on Microbial Biofilms", National Institutes of Health, PA Number: PA-03-047, Dec. 20, 2002). Biofilms are involved in health conditions such as urinary tract infections, cystitis, lung infections, skin infections, mucous membrane infections, sinus infections, ear infections, acne, dental caries, periodontitis, nosocomial infections, open wounds, and chronic wounds. Additionally, biofilms can form on medical devices such as: urinary tract prostheses; urinary tract catheters; peritoneal membrane catheters, peritoneal dialysis catheters, indwelling catheters for hemodialysis and for chronic administration of chemotherapeutic agents (Hickman catheters); cardiac implants such as pacemakers, prosthetic heart valves, ventricular assist devices, and synthetic vascular grafts and stents; prostheses; percutaneous sutures; and tracheal and ventilator tubing.

Bacteria growing in biofilms exhibit increased tolerance to antibiotics and antibacterial agents and are very difficult to substantially reduce or eliminate. Bacteria within biofilms have increased tolerance (up to 1000-fold higher) to antibacterial compounds than bacteria not within biofilms, even though these same bacteria are sensitive to these agents if grown under planktonic conditions ("Research on Microbial Biofilms", National Institutes of Health, PA Number: PA-03-047, Dec. 20, 2002). Bacteria grown in biofilms are also physiologically distinct from the same bacteria grown under planktonic conditions. The bacteria in biofilms are stratified into different metabolic states depending on where in the biofilm they reside and thus display different phenotypes compared to their free-living counterparts. Another theory behind the antimicrobial tolerance of bacteria in biofilms is the protective role of the EPS. The EPS can be visualized as a "mesh" or a network that can physically prevent foreign agents (e.g., antibacterial agents) from reaching the bacteria. Because of the EPS, altered metabolic states and acquired resistance factors, biofilms have a multifactorial tolerance to antibacterial agents and antibiotics. Moreover, most of the antibacterial formulations are water-based preparations, making it even harder for the antibacterial active to penetrate the biofilm network due to high surface tension of water molecules.

Wounds, mucous membrane lesions, and skin lesions are especially susceptible to bacterial infection. From a microbiological perspective, the primary function of normal, intact skin is to control microbial populations that live on the skin surface and to prevent underlying tissue from becoming colonized and invaded by potential pathogens. Exposure of subcutaneous tissue, such as a wound, mucous membrane lesion, or skin lesion, provides a moist, warm and nutritious environment that is conducive to microbial colonization and proliferation. Since wound colonization is mostly polymicrobial, involving numerous microorganisms that are potentially pathogenic, any wound, mucous membrane lesion, or skin lesion is at some risk of becoming infected.

Wounds often have multiple barriers to healing. Wound healing and infection is influenced by the relationship between the ability of bacteria to create a stable, prosperous community within a wound environment and the ability of the host to control the bacterial community. Since bacteria are rapidly able to form their own protective microenvironment, i.e., a biofilm, following their attachment to a surface, the ability of the host to control these organisms is likely to decrease as the biofilm community matures, ultimately affecting the ability of the wound to heal. Wounds in which healing is delayed, i.e., chronic wounds, are of particular concern with respect to biofilm formation. While biofilms are not present in all bacterial infections, some have linked biofilms to chronic wounds (Mertz, 2003, Wounds, 15: 1-9). Wounds such as diabetic foot ulcers, venous ulcers, arterial ulcers, decubitus ulcers, stasis ulcers, pressure ulcers, and burns are examples of wounds which may become chronic wounds. Bacterial biofilms in chronic wounds are generally not resolved by the host's immune system and these biofilms have an increased tolerance to systemic and topical antibacterial/antibiotic agents. Accordingly, bacterial biofilm infections in chronic wounds are very difficult to substantially reduce or eliminate.

Particularly virulent organisms in wounds, mucous membrane lesions, and skin lesions are gram-positive bacteria such as *staphylococcus* spp., *streptococcus* spp., and *enterococci* spp. Biofilms of *Staphylococcus aureus*, including resistant strains such as methicillin resistant *Staphylococcus Aureus* (MRSA), have become increasingly problematic in wounds, skin lesions, and mucous membrane lesions. These organisms, especially MRSA, can reside in the anterior nares and cause lesions in the nose which can also spread to other parts of the body, causing skin lesions and mucous membrane lesions at those sites. The gram-negative bacteria *Pseudomonas aeruginosa* is also a particularly virulent organism in wounds (Bjarnsholt, 2008, Wound Repair and Regeneration; and Jacobsen, 2011, International Wound Journal).

In recent years, there have been numerous efforts to use various antibiotics and antibacterial agents for the treatment of mucous membrane lesions, skin lesions, and chronic wounds, many of which are infected or contaminated with bacterial biofilms. These agents are of varying chemical compounds and include, among others, peptides such as vancomycin, and antibacterial agents such as mupirocin, iodine compounds, and silver/silver ions. However, many bacteria have become increasingly resistant to these compounds.

Thus, there is a need for safe and effective compositions which can reduce or eliminate bacterial biofilms in wounds, mucous membrane lesions, and skin lesions, and on other biological and non-biological surfaces.

SUMMARY OF THE INVENTION

The present invention provides a solution to the aforementioned limitations and deficiencies in the art relating to bacterial biofilms. In particular, the solution is premised on the use of thermolysin and compositions comprising thermolysin to reduce or eliminate bacterial biofilms on surfaces including biological and non-biological surfaces. In one aspect of the invention, disclosed are methods for treating wounds, mucous membrane lesions, skin lesions, and/or other biological surfaces infected or contaminated with bacterial biofilms by administering thermolysin or compositions comprising thermolysin to the surfaces. In another aspect, disclosed are methods for preventing, reducing, or eliminating bacterial biofilms on non-biological surfaces by administering thermolysin or compositions comprising thermolysin to the surfaces. In still another aspect, disclosed are compositions comprising thermolysin useful for the reduction or elimination of bacterial biofilms present on biological and non-biological surfaces.

Also disclosed in the context of the present invention are embodiments 1 to 51. Embodiment 1 is a method of treating a wound, mucous membrane lesion, or skin lesion infected or contaminated with a bacterial biofilm, the method comprising topically administering to the wound, mucous membrane lesion, or skin lesion a composition comprising thermolysin, wherein the bacterial biofilm is reduced or eliminated. Embodiment 2 is the method of embodiment 1, wherein the composition further comprises a carrier. Embodiment 3 is the method of any one of embodiments 1 to 2, wherein the bacterial biofilm is a gram-positive bacterial biofilm. Embodiment 4 is the method of embodiment 3, wherein the gram-positive bacterial biofilm is a *Staphylococcus* sp. Embodiment 5 is the method of embodiment 4, wherein the *Staphylococcus* sp. is *Staphylococcus aureus*. Embodiment 6 is the method of embodiment 5, wherein the *Staphylococcus* sp. is methicillin resistant *Staphylococcus aureus* (MRSA). Embodiment 7 is the method of any one of embodiments 1 to 2, wherein the bacterial biofilm is a gram-negative bacterial biofilm. Embodiment 8 is the method of embodiment 7, wherein the gram-negative bacterial biofilm is a *Pseudomonas* sp. Embodiment 9 is the method of embodiment 8, wherein the *Pseudomonas* sp. is *Pseudomonas aeruginosa*. Embodiment 10 is the method of any one of embodiments 1 to 9, wherein the wound is a chronic wound. Embodiment 11 is the method of embodiment 10, wherein the chronic wound is a diabetic foot ulcer, venous ulcer, arterial ulcer, decubitus ulcer, stasis ulcer, pressure ulcer, or burn. Embodiment 12 is the method of any one of embodiments 1 to 9, wherein the skin lesion or mucous membrane lesion is a blister, ulceration, abrasion, wart, abscess, scrape, or infection. Embodiment 13 is the method of any one of embodiments 1 to 12, wherein the concentration of thermolysin is at an amount that results in a reduction or elimination of the bacterial biofilm on the wound, mucous membrane lesion, or skin lesion. Embodiment 14 is the method of any one of embodiment 1 to 13, wherein the concentration of thermolysin is at least 0.00001 mg/mL, at least 0.0001 mg/mL, at least 0.001 mg/mL, at least 0.01 mg/mL, at least 0.1 mg/mL, at least 1.0 mg/mL, or at least 10 mg/mL. Embodiment 15 is the method of any one of embodiments 2 to 14, wherein the carrier is a lotion, solution, suspension, liquid, emulsion, cream, gel, ointment, paste, aerosol spray, aerosol foam, non-aerosol spray, non-aerosol foam, film, or sheet. Embodiment 16 is the method of embodiment 15, wherein the carrier is a pharmaceutically acceptable carrier. Embodiment 17 is the method of any one of embodiments 1 to 16, wherein the composition further comprises an antibacterial agent. Embodiment 18 is a method of reducing or eliminating a bacterial biofilm on a biological surface, the method comprising administering to the biological surface a composition comprising thermolysin. Embodiment 19 is the method of embodiment 21, wherein the composition further comprises a carrier. Embodiment 20 is the method of any one of embodiments 18 to 19, wherein the biological surface is a wound. Embodiment 21 is the method of embodiment 20, wherein the wound is a chronic wound. Embodiment 22 is the method of embodiment 21, wherein the chronic wound is a diabetic foot ulcer, venous ulcer, arterial ulcer, decubitus ulcer, stasis ulcer, pressure ulcer, or burn. Embodiment 23 is the method of any one of embodiments 18 to 19, wherein the biological surface is a skin lesion, or mucous membrane lesion. Embodiment 24 is the method of embodiment 23, wherein the skin lesion or mucous membrane lesion, is a blister, ulceration, abrasion, wart, abscess, scrape, or infection. Embodiment 25 is the method of any one of embodiments 18 to 19, wherein the biological surface is an internal organ, a body cavity, an oral cavity, a bone tissue, a muscle tissue, a nerve tissue, an ocular tissue, a urinary tract tissue, a lung tissue, a trachea tissue, a sinus tissue, an ear tissue, a dental tissue, a gum tissue, a nasal tissue, a vascular tissue, a cardiac tissue, an epithelium tissue, an epithelial lesion, a vaginal tissue, or a peritoneal tissue. Embodiment 26 is the method of any one of embodiments 18 to 25, wherein the bacterial biofilm is a gram-positive bacterial biofilm. Embodiment 27 is the method of embodiment 26, wherein the gram-positive bacterial biofilm is a *Staphylococcus* sp. Embodiment 28 is the method of embodiment 27, wherein the *Staphylococcus* sp. is *Staphylococcus aureus*. Embodiment 29 is the method of embodiment 28, wherein the *Staphylococcus* sp. is methicillin resistant *Staphylococcus aureus* (MRSA). Embodiment 30 is the method of any one of embodiments 18 to 25, wherein the bacterial biofilm is a gram-negative bacterial biofilm. Embodiment 31 is the method of embodiment 30, wherein the gram-negative bacterial biofilm is a *Pseudomonas* sp. Embodiment 32 is the method of embodiment 31, wherein the *Pseudomonas* sp. is *Pseudomonas aeruginosa*. Embodiment 33 is the method of any one of embodiments 18 to 32, wherein the concentration of the thermolysin is at an amount that results in a reduction or elimination of the bacterial biofilm on the biological surface. Embodiment 34 is the method of any one of embodiment 18 to 33, wherein the concentration of thermolysin is at least 0.00001 mg/mL. Embodiment 35 is the method of any one of embodiments 19 to 34, wherein the carrier is a pharmaceutical carrier. Embodiment 36 is the method of embodiment 35, wherein the pharmaceutical carrier is a lotion, solution, suspension, liquid, emulsion, cream, gel, ointment, paste, aerosol spray, aerosol foam, non-aerosol spray, non-aerosol foam, film, or sheet. Embodiment 37 is a method of reducing or eliminating a bacterial biofilm on a non-biological surface, the method comprising administering to the non-biological surface a composition comprising thermolysin. Embodiment 38 is the method of embodiment 37, wherein the composition further comprises a carrier suitable for application to a non-biological surface. Embodiment 39 is the method of an of embodiments 37 or 38, wherein the non-biological surface is the surface of a medical device. Embodiment 40 is the method of embodiment 39, wherein the medical device is a urinary tract prosthesis, urinary tract catheter, peritoneal membrane catheter, peritoneal dialysis catheter, indwelling catheter for hemodialysis, indwelling catheter for administration of chemotherapeutic agents, cardiac implant, pacemaker, prosthetic heart valve, ventricular assist device, synthetic vascular graft, synthetic vascular stent, prosthesis, percutaneous suture, tracheal tubing, or ventilator tubing. Embodiment 41 is the method of any one of embodiments 37 to 40, wherein the concentration of the thermolysin is at an amount that results in a reduction or elimination of the bacterial biofilm on the non-biological surface. Embodiment 42 is the method of any one of embodiment 37 to 41, wherein the concentration of thermolysin is at least 0.00001 mg/mL. Embodiment 43 is an article of manufacture comprising a surface coated with a composition comprising thermolysin. Embodiment 44 is the article of manufacture of embodiment 43, wherein the article of manufacture is a medical device. Embodiment 45 is the article of manufacture of embodiment 44, wherein the medical device is a urinary tract prosthesis, urinary tract catheter, peritoneal membrane catheter, peritoneal dialysis catheter, indwelling catheter for hemodialysis, indwelling catheter for administration of chemotherapeutic agents, cardiac implant, pacemaker, prosthetic heart valve, ventricular assist device, synthetic vascular graft, synthetic vascular stent, prosthesis, percutaneous suture, tracheal tubing, or ventilator tubing. Embodiment 46 is the article of manufacture of any one of embodiments 43 to 45, wherein a biofilm is not present on the surface of the article of manufacture prior to coating with the composition. Embodiment 47 is the article of manufacture of any one of embodiments 43 to 45, wherein a biofilm is present on the surface of the article of manufacture prior to coating the surface with the composition. Embodiment 48 is a method of treating a surface of an article of manufacture to prevent or reduce the likelihood of biofilm formation on said surface, the method comprising coating the surface with a composition comprising thermolysin. Embodiment 49 is the method of embodiment 48, wherein the article of manufacture is a medical device. Embodiment 50 is the method of embodiment 49, wherein the medical device is a urinary tract prosthesis, urinary tract catheter, peritoneal membrane catheter, peritoneal dialysis catheter, indwelling catheter for hemodialysis, indwelling catheter for administration of chemotherapeutic agents, cardiac implant, pacemaker, prosthetic heart valve, ventricular assist device, synthetic vascular graft, synthetic vascular stent, prosthesis, percutaneous suture, tracheal tubing, or ventilator tubing. Embodiment 51 is the method of embodiment 48, wherein the article of manufacture is an electrospun polymer fiber or nanofiber, and wherein the composition comprising thermolysin is covalently attached to or adsorbed onto the electrospun polymer fiber or nanofiber.

Unless otherwise specified, the percent values expressed herein are weight by weight and are in relation to the weight of the total composition. By way of example, 10 grams of component in 100 grams of material is 10 wt. % of component.

The terms "reduce", "reduced", "reducing", or "reduction" in the context of a bacterial biofilm means a reduction in the count of bacteria in the biofilm.

The terms "treat," "treated," "treatment", or "treating," in the context of treating a bacterial biofilm on a biological surface, or treating a mucous membrane lesion, a wound, or a skin lesion, means any measurable reduction or complete elimination of the bacterial biofilm, and/or a therapeutic improvement of the mucous membrane lesion, wound, or skin lesion.

The term "effective," in the context of treating a bacterial biofilm or treating a wound, mucous membrane lesion, or skin lesion means adequate to accomplish a desired, expected, or intended result, including a therapeutic improvement.

The terms "eliminate", "eliminated", "eliminating", or "elimination" in the context of a bacterial biofilm means total eradication of the bacteria present in the biofilm.

The terms "prevent", "prevented", or "preventing" in the context of a bacterial biofilm means reduced likelihood or complete prevention of bacterial biofilm formation on a surface such as a biological or a non-biological surface that has been coated with a composition of the present invention.

The term "wound" as used herein means an external wound of the skin or mucous membranes and includes chronic and acute wounds.

The term "lesion" as used herein means a region on a bodily tissue that has suffered damage through injury or disease.

The terms "about" or "approximately" are defined as being close to as understood by one of ordinary skill in the art, and in one non-limiting embodiment the terms are defined to be within 10%, preferably within 5%, more preferably within 1%, and most preferably within 0.5%.

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The use of the word "a" or "an" when used in conjunction with the terms "comprising", "having", "including", or "containing" (or any variations of these words) may mean "one," but it is also consistent with the meaning of "one or more," "at least one," and "one or more than one."

The compositions and methods for their use can "comprise," "consist essentially of," or "consist of" any of the ingredients or steps disclosed throughout the specification.

It is contemplated that any embodiment discussed in this specification can be implemented with respect to any method or composition of the invention, and vice versa. Furthermore, compositions of the invention can be used to achieve methods of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

The present invention relates to methods and compositions useful for the reduction, elimination, or prevention of bacterial biofilms and/or growth of such biofilms on surfaces. In particular, the present invention provides compositions comprising thermolysin which exhibit activity against bacterial biofilms, and methods of administering these compositions to biological and non-biological surfaces infected or contaminated with bacterial biofilms thereby effectively reducing or eliminating the bacterial biofilms. Additionally, surfaces susceptible to biofilm formation (e.g., medical devices) can be treated with such compositions to prevent biofilm formation. In one aspect, the present invention relates to methods and compositions useful for the treatment of wounds, skin lesions, mucous membrane lesions, and other biological surfaces infected or contaminated with bacterial biofilms. In another aspect, the present invention relates to methods and compositions useful for the reduction, elimination, or prevention of bacterial biofilms and/or growth of such biofilms on non-biological surfaces such as medical devices. Without being bound by theory, thermolysin may disrupt and/or digest the extracellular polymeric substance (EPS) matrix of the bacterial biofilm thereby reducing, eliminating, and/or preventing biofilm growth or formation. Thermolysin may also exhibit bactericidal activity on the bacteria.

I. Compositions

The compositions of the present invention comprise thermolysin. Thermolysin is a thermostable metalloproteinase made by a fermentation process from a bacterial species called *Bacillus thermoproteolyticus rokko* that cleaves at the N-terminus of the hydrophobic residues leucine, phenylalanine, valine, isoleucine, alanine, and methionine. Amano Japan is a manufacturer and supplier of thermolysin. The thermolysin can be isolated and/or purified. The CAS No. for thermolysin is 9073-78-3.

The concentration of the thermolysin in the composition is at an amount that results in a reduction or elimination of a bacterial biofilm on a surface when the composition is administered to the surface. In various embodiments, the concentration of thermolysin in the compositions of the invention can be at least 0.00001 mg/mL, or at least 0.0001 mg/mL, or at least 0.001 mg/mL, or at least 0.01 mg/mL, or at least 0.1 mg/mL, or at least 1.0 mg/mL, or at least 10 mg/mL, or from 0.00001 mg/mL to 10 mg/mL, or from 0.0001 mg/mL to 10 mg/mL, or from 0.001 mg/mL to 10 mg/mL, or from 0.01 mg/mL to 10 mg/mL, or from 0.1 mg/mL to 10 mg/mL, or from 1.0 mg/mL to 10 mg/mL, or from 0.00001 mg/mL to 1.0 mg/mL or from 0.0001 mg/mL to 1.0 mg/mL, or from 0.001 mg/mL to 1.0 mg/mL, or from 0.01 mg/mL to 1.0 mg/mL, or from 0.1 mg/mL to 1.0 mg/mL, or from 0.00001 mg/mL to 0.1 mg/mL or from 0.0001 mg/mL to 0.1 mg/mL, or from 0.001 mg/mL to 0.1 mg/mL, or from 0.01 mg/mL to 0.1 mg/mL, or from 0.00001 mg/mL to 0.01 mg/mL, or from 0.0001 mg/mL to 0.01 mg/mL, or from 0.001 mg/mL to 0.01 mg/mL, or from 0.00001 mg/mL to 0.001 mg/mL, or from 0.0001 mg/mL to 0.001 mg/mL, or from 0.00001 mg/mL to 0.001 mg/mL, or can be 0.00001 mg/mL, or 0.0001 mg/mL, or 0.001 mg/mL, or 0.01 mg/mL, or 0.1 mg/mL, or 1.0 mg/mL, or 10 mg/mL.

The compositions of the invention can comprise an acceptable carrier such as a carrier suitable for application to biological surfaces including wounds, mucous membranes, skin, organs and other biological tissues; or a carrier suitable for application to non-biological surfaces including medical devices. The carrier can be a pharmaceutically acceptable carrier. The carrier can be a carrier suitable for topical delivery and treatment. Non-limiting examples of carriers include lotions, solutions, suspensions, liquids, emulsions, creams, gels, ointments, pastes, aerosol sprays, aerosol foams, non-aerosol sprays, non-aerosol foams, films, powders, and sheets. The compositions can be impregnated in gauzes, bandages, or other wound dressing materials. Non-limiting examples of carriers suitable for topical treatment of skin, mucous membranes and wounds include those carriers disclosed in U.S. Pat. No. 6,399,092, herein incorporated by reference, which are anhydrous, hydrophilic carriers comprising a super absorbent polymer, an antimicrobial agent, and poloxamers and/or polyols. The carriers disclosed in US publication 2016/0008293, herein incorporated by reference, which are dissolvable gel-forming film compositions with a water content of less than 15% w/w comprising a water-soluble cellulose ether, a hydrophilic rheological modifying agent, and a proteolytic enzyme, wherein the gel-forming film is capable of forming a hydrogel when in contact with water or other aqueous medium, are suitable carriers for topical treatment of skin, mucous membranes, and wounds. The carriers disclosed in US publication 2013/0045196, herein incorporated by reference, which are compositions comprising a dispersed phase comprising a liquid hydrophilic polyol and a proteolytic enzyme, and a continuous phase comprising a hydrophobic base, are suitable carriers for topical treatment of skin, mucous membranes, and wounds. The carriers disclosed in US publication 2015/0283217, herein incorporated by reference, which are hydrogel compositions comprising a hydrophilic gelling agent that includes a nonionic cellulose ether and thermolysin, are suitable carriers for topical treatment of skin, mucous membranes, and wounds. The carriers disclosed in U.S. Pat. No. 7,785,584, herein incorporated by reference, which are spray-on compositions comprising a cryptoanionic surfactant emulsifier comprising an alkoxylated fatty alcohol and mono and diester phosphates; at least one wound healing agent, emollient, humectant, preservative, or anti-microbial; and a proteolytic enzyme, are suitable carriers for topical treatment of skin, mucous membranes, and wounds.

Other non-limiting examples of suitable carriers include petrolatum-based ointments, polyethylene glycol-based ointments and gels, poloxamer based ointments and gels, anhydrous compositions, aqueous-based compositions, hydrophobic compositions, and/or hydrophilic compositions.

The compositions of the invention may further comprise functional ingredients suitable for use in compositions for application to biological surfaces or non-biological surfaces. Non-limiting examples include absorbents, super absorbents, antibacterial agents, antioxidants, binders, buffering agents, bulking agents, chelating agents, colorants, biocides, deodorant agents, emulsion stabilizers, film formers, fragrance ingredients, humectants, lytic agents, enzymatic agents, opacifying agents, oxidizing agents, pH adjusters, plasticizers, preservatives, reducing agents, emollient skin conditioning agents, humectant skin conditioning agents, moisturizers, surfactants, emulsifying agents, cleansing agents, foaming agents, hydrotopes, solvents, suspending agents, viscosity control agents (rheology modifiers), viscosity increasing agents (thickeners), and/or propellants. Listings and monographs of suitable functional ingredients are disclosed in McCutcheon's Vol. 1 Emulsifiers & Detergents, and Vol. 2 Functional Materials, 2001, herein incorporated by reference.

The compositions of the invention can further comprise pharmaceutically active ingredients, cosmetically active ingredients, vulnerary agents, wound healing agents, antibiotics, anti-fungal agents, antiseptics, cleansing agents, and antibacterial agents. The compositions can be sterile or preserved with preservatives.

Various antibacterial agents are suitable for use with the present invention. Suitable antibacterial agents include silver compounds such as the following non-limiting examples: elemental silver, silver nanoparticles, silver zeolite, silver sulfadiazine, ionized silver, and silver salts such as silver chloride and silver nitrate. Other suitable antibacterial agents include iodine compounds such as the following non-limiting examples: iodine, tincture of iodine, Lugol's iodine solution, iodides, iodine topical solution, iodine complexed with phosphate ester of alkylaryloxy polyethylene, iodoquinol, undecoylium chloride-iodine, nonylphenoxypolyethanol-iodine complex, and iodophors such as povidone-iodine (PVP-iodine), polyvinyl alcohol-iodine, polyvinyl oxazolidone-iodine, polyvinyl imidazole-iodine, polyvinyl morpholone-iodine, and polyvinyl caprolactam-iodine, nonylphenolethoxylate-iodine, soluble starch-iodine, betacyclodextrin-iodine, polyoxyethylenepolyoxypropylene condensate-iodine, ethoxylated linear alcohol-iodine, and cadexomer-iodine. Additional non-limiting examples of suitable antibacterial agents include: chlorhexidine and its salts dihydrochloride, diacetate, and digluconate; quaternary ammonium compounds such as benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride and domiphen bromide; chlorine containing compounds such as sodium hypochlorite, calcium hypochlorite, and chlorine dioxide; hydrogen peroxide; benzoic acid and its salts; benzoyl peroxide; benzyl alcohol; bispyrithione salts; boric acid; camphorated metacresol; camphorated phenol; chlorobutanol; cloflucarban; dapsone; dehydroacetic acid and its salts; ethyl alcohol; hexachlorophene; hexitidine; hexylresorcinol; hydroxybenzoic acid and its salts; isopropyl alcohol; mafenide acetate; magnesium pyrithione; merbromin; mercufenol chloride; methylparaben; metronidazole and its derivatives; mupirocin and its salts; nitrofurazone; n-Propanol; organic peroxides; p-chloro-m-xylenol; phenol; phenoxyethanol; phenyl alcohol; phenyl ethyl alcohol; selenium sulfide; sodium oxychlorosene; sodium sulfacetmide; sorbic acid and its salts; sulfur; tetrachlorosalicylanilide; thymol; tribromsalan; triclocarbon; triclosan; and zinc pyrithione. Antibacterial peptides and antibiotics are also suitable antibacterial agents. In some embodiments, the compositions of the invention further comprise one or more antibacterial agents. In other embodiments, the compositions of the invention further comprise one or more antibiotic agents. In other non-limiting embodiments, the compositions of the invention may not include any of the aforementioned antibacterial agents and/or antibiotic agents such that thermolysin is the primary or sole active in treating the biofilm.

The compositions of the present invention may be packaged in any suitable package configuration. Non-limiting examples include bottles, lotion pumps, toddles, tubes, jars, non-aerosol pump sprayers, aerosol containers, pouches, and/or packets. The packages may be configured for single-use or multiple-use administration.

A. Manufacture

The compositions of the invention may be manufactured by methods and equipment known in the art for manufacture of pharmaceutical and topical products, and products designed for application to non-biological surfaces, such as medical devices. Such methods include, but are not limited to the use of mechanical mixers including LIGHTNIN propeller mixers; COWLES dissolvers; SILVERSON dispersers; counter-rotating side-scrapping mixers; homogenizers and dispersers, including in-line or in-tank rotor-stator homogenizers; and mills, including 3-roll mills, ointment mills, or rotor-stator mills. "All-in-one" vacuum mixing systems that have a rotating side-scrapping mixer plus an in-tank homogenizer may also be used. Such mixers include, but are not limited to OLSA mixers, FRYMA-KORUMA mixers, and LEE TRI-MIX TURBO-SHEAR kettles. The compositions of the invention can be manufactured from small laboratory scale batches to full-scale production batches.

II. Bacterial Biofilms

The compositions of the invention are suitable for the reduction of bacteria in and/or elimination of both gram-positive and gram-negative bacterial biofilms. The compositions can also be used to prevent such biofilm formation on surfaces such as medical devices. Non-limiting examples of gram-positive bacteria include *Staphylococcus* spp., such as *Staphylococcus aureus*, methicillin resistant *Staphylococcus aureus* (MRSA), and *Staphylococcus epidermidis; Streptococcus* spp, such as *Streptococcus pneumonia; Bacillus* spp.; *Listeria monocytogenes; enterococci* spp.; and lactic acid bacteria, such as *Lactobacillus plantarum* and *Lactococcus lactis*. Non-limiting examples of gram-negative bacteria include *Pseudomonas* spp., such as *Pseudomonas aeruginosa*; and *Escherichia coli*.

A. In-Vitro Biofilm Model

An in-vitro biofilm model was used to evaluate the biofilm efficacy of the formulations of the invention against bacterial biofilms. Bacteria are spotted onto a collagen matrix resting on a filter on a blood agar plate and incubated to allow biofilm formation. The model mimics in-vivo wound biofilms in that nutrients are provided from below the biofilm while topical treatments are applied at the air interface above. This in-vitro model and methodology is disclosed in the poster presentation, A Versatile In Vitro Biofilm Model Using Two Wound Pathogens to Screen Formulations, Van der Kar, et al., presented at the 2010 Wound Healing Society Annual Meeting, Poster BRC09, on Apr. 18, 2010 in Orlando, Fla., and is herein incorporated by reference. Further in-vitro biofilm models and methodologies are disclosed in the following publications, all of which are herein incorporated by reference: Penetration of Rifampin through *Staphylococcus epidermidis* Biofilms, Zheng, et al., Antimicrobial Agents and Chemotherapy, March 2002, p. 900-903; Oxygen Limitation Contributes to Antibiotic Tolerance of *Pseudomonas aeruginosa* in Biofilms, Borriello et al., Antimicrobial Agents and Chemotherapy, July 2004, p. 2659-2664; and Heterogeneity in *Pseudomonas aeruginosa* Biofilms Includes Expression of Ribosome Hibernation Factors in the Antibiotic-Tolerant Subpopulation and Hypoxia-Induced Stress Response in the Metabolically Active Population, Williamson et al., Journal of Bacteriology, February 2012, p. 2062-2073.

III. Methods of Use and Treatment

The compositions of the invention are useful for the reduction of bacteria in and/or elimination of bacterial biofilms on biological and non-biological surfaces, and are also useful for treatment of wounds, skin lesions, mucous membrane lesions, and other biological surfaces infected or contaminated with bacterial biofilms. The compositions can also be used to prevent biofilm growth or formation on surfaces susceptible of growing or forming biofilms (e.g., a surface of a medical device). Disclosed are methods of treating a wound, mucous membrane lesion, skin lesion, or other biological surface infected or contaminated with a bacterial biofilm, the method comprising administering to the wound, mucous membrane lesion, skin lesion, or biological surface a composition comprising thermolysin, wherein the bacterial biofilm is reduced or eliminated. Subsequently following treatment with the composition, other compositions comprising pharmaceutically active ingredients, cosmetically active ingredients, vulnerary agents, wound healing agents, antibiotics, anti-fungal agents, antiseptic agents, cleansing agents, and/or antibacterial agents, can be administered to the wound, mucous membrane lesion, skin lesion, or biological surface for further treatment.

A. Biological Surfaces

The compositions of the invention are useful for reducing or eliminating a bacterial biofilm on a biological surface by administering the compositions to the biological surface. Non-limiting examples of biological surfaces include wounds (including chronic and acute wounds), skin lesions, skin, mucous membranes, mucous membrane lesions, internal organs, body cavity, oral cavity, bone tissue, muscle tissue, nerve tissue, ocular tissue, urinary tract tissue, lung and trachea tissue, sinus tissue, ear tissue, dental tissue, gum tissue, nasal tissue, vascular tissue, cardiac tissue, epithelium, and epithelial lesions, and peritoneal tissue. Non-limiting examples of chronic wounds include diabetic foot ulcers, venous ulcers, arterial ulcers, decubitus ulcers, stasis ulcers, pressure ulcers, and burns. Non-limiting examples of acute wounds include cuts and surgical wounds. Non-limiting examples of skin lesions and mucous membrane lesions include blisters, ulcers, abrasions, warts, abscesses, scrapes, and skin and mucosal infections such as staph or MRSA infections. Examples of skin lesions and mucous membrane lesions are disclosed in "Description of Skin Lesions", MacNeal, Robert J., the on-line Merck Manual Professional Version, March 2013, http://www.merckmanuals.com/professional/dermatologic-disorders/approach-to-the-dermatologic-patient/description-of-skin-lesions herein incorporated by reference. Skin lesions can appear on the epidermis, lips, ear canal, scalp, cuticle, nail bed, or genitalia. Mucous membrane lesions can appear on the oral mucosa, nasal mucosa, penile and vaginal mucosa, or anus.

B. Topical Treatment of Wounds

The compositions of the invention are useful for the treatment of wounds, including chronic wounds and acute wounds, infected or contaminated with bacterial biofilms, by topically administering the compositions to the wound. Non-limiting examples of chronic wounds include diabetic foot ulcers, venous ulcers, arterial ulcers, decubitus ulcers, stasis ulcers, pressure ulcers, and burns. Non-limiting examples of acute wounds include cuts and surgical wounds. In some embodiments, the wound includes eschar and/or necrotic tissue and is in need of debridement. In various embodiments, the compositions serve a dual function and further debride wounds that are in need of debridement in addition to reducing or eliminating a bacterial biofilm present in the wounds. In other embodiments, the wound does not include eschar and/or necrotic tissue and is not in need of debridement.

C. Topical Treatment of Skin Lesions and Mucous Membrane Lesions

The compositions of the invention are useful for the treatment of skin lesions or mucous membrane lesions infected or contaminated with bacterial biofilms by topically administering the compositions to the skin lesion or mucous membrane lesions. Non-limiting examples of skin lesions and mucous membrane lesions include blisters, ulcerations, abrasions, warts, abscesses, scrapes, and skin and mucosal infections such as staph or MRSA infections. Skin lesions can appear on the epidermis, lips, ear canal, scalp, cuticle, nail bed, or genitalia. Mucous membrane lesions can appear on the oral mucosa, nasal mucosa, penile and vaginal mucosa, or anus. In some embodiments, the mucous membrane lesion or skin lesion includes eschar and/or necrotic tissue and is in need of debridement. In various embodiments, the compositions serve a dual function and further debride lesions that are in need of debridement in addition to reducing or eliminating a bacterial biofilm present in the lesions. In other embodiments, the mucous membrane lesion or skin lesion does not include eschar and/or necrotic tissue and is not in need of debridement.

D. Treatment of other Biological Surfaces

The compositions of the invention are useful for the treatment of other biological surfaces infected or contaminated with bacterial biofilms by administering the compositions to the biological surface. Non-limiting examples of other biological surfaces include internal organs, body cavity, oral cavity, bone tissue, muscle tissue, nerve tissue, ocular tissue, urinary tract tissue, lung tissue, trachea tissue, sinus tissue, ear tissue, dental tissue, gum tissue, nasal tissue, vascular tissue, cardiac tissue, epithelium tissue, epithelial lesions, vaginal tissue, and/or peritoneal tissue.

E. Non-Biological Surfaces

The compositions of the invention are useful for reducing or eliminating a bacterial biofilm on a non-biological surface, such as the surface of an article of manufacture such as a medical device, by administering the compositions to the non-biological surface. The compositions can also be used to prevent biofilm growth or formation on these non-biological surfaces. Such surfaces can be susceptible to biofilm growth or formation due to their exposure to human tissue and/or wounds. Non-limiting examples of medical devices include urinary tract prostheses; urinary tract catheters, peritoneal membrane catheters, peritoneal dialysis catheters, indwelling catheters for hemodialysis and for chronic administration of chemotherapeutic agents (Hickman catheters); cardiac implants such as pacemakers, prosthetic heart valves, ventricular assist devices, and synthetic vascular grafts and stents; prostheses; percutaneous sutures; and tracheal and ventilator tubing.

The surface of an article of manufacture, including medical devices, can be coated with the compositions of the inventions in order to prevent the formation of bacterial biofilms on the surface of the article of manufacture. Additional suitable articles of manufacture include electrospun polymer fibers and/or nanofibers such as polymethylmethacrylate (PMMA) electrospun fibers. In some embodiments, a bacterial biofilm is not present on the surface prior to coating. In other embodiments, a bacterial biofilm is present on the surface prior to coating. Various methods known in the art for coating an article of manufacture with thermolysin can be employed such as spraying or dipping. Additional methods of coating can also include covalent attachment or adsorption of thermolysin to a non-biological surface, including surfaces of electrospun polymer fibers and/or nanofibers. Methods of covalently attaching or adsorbing proteins and enzymes to electrospun polymer fibers and/or nanofibers are disclosed in Ahn et al., Robust trypsin coating on electrospun polymer nanofibers in rigorous conditions and its uses for protein digestion, Biotechnol. Bioeng. December 2010; 107: 917-923, and Polini et al., Collagen-functionalised electrospun polymer fibers for bioengineering applications, Soft Matter, February 2010, 6, 1668-1674, both of which are herein incorporated by reference. In one embodiment, disclosed is a method of treating a surface of an article of manufacture to prevent or reduce the likelihood of biofilm formation on said surface, the method comprising coating the surface with a composition comprising thermolysin. In another embodiment, the article of manufacture is an electrospun polymer fiber or nanofiber and the composition comprising thermolysin is covalently attached to or adsorbed onto the electrospun polymer fiber or nanofiber.

EXAMPLES

Example 1

In-Vitro Biofilm Study with Thermolysin and Collagenase

Figure 1:
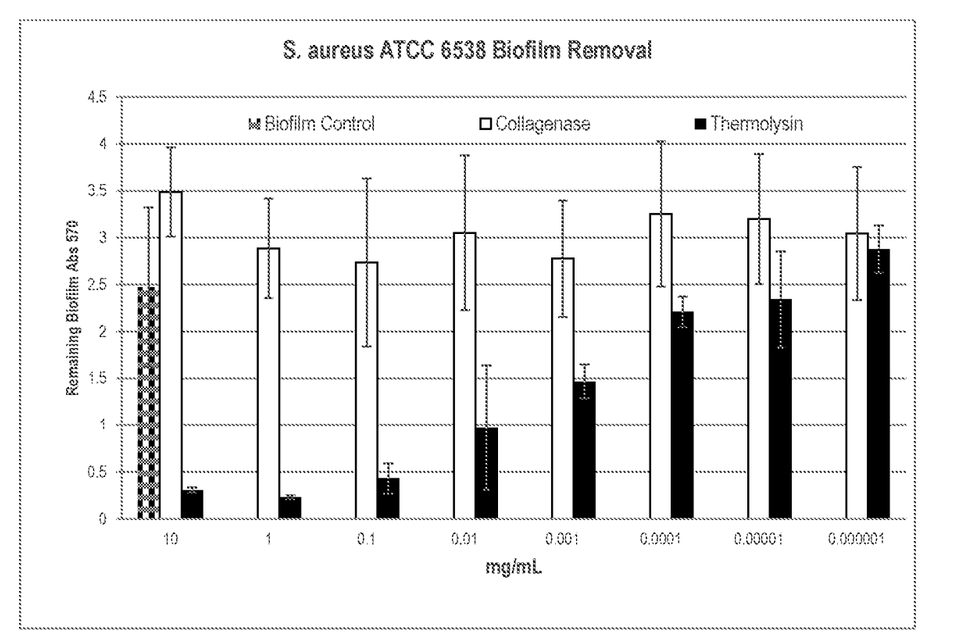
FIG. 1. A graph showing the effect of thermolysin on a *S. aureus* bacterial biofilm in-vitro when compared with collagenase and a Control.

An in-vitro assay was performed to demonstrate the bacterial biofilm reduction capabilities of thermolysin. In this assay, S. aureus ATCC 6538 was suspended in a growth media of tryptic soy broth supplemented with 0.25% glucose for optimal bacterial biofilm formation. The suspension was transferred to the wells of sterile 96 well plates and incubated for 22 hours at 37° C. with one change of media. After formation of the bacterial biofilm, the growth media was replaced with solutions of thermolysin dissolved in growth media at various concentrations and solutions of collagenase dissolved in growth media at the same concentrations (enzyme concentrations were 0.000001 mg/mL, 0.00001 mg/mL, 0.0001 mg/mL, 0.001 mg/mL, 0.01 mg/mL, 0.1 mg/mL, 1.0 mg/mL, and 10 mg/mL). After 16 hours, the remaining attached bacteria were quantified by aspirating the enzyme solutions (enzyme+growth media) and washing the plate thoroughly followed by crystal violet staining and recording the absorbance at 570 nm. A Control without enzyme was also tested. The crystal violet stained the remaining attached bacteria. A decreased absorbance compared to the Control indicates a reduction of attached bacteria meaning a reduction of the bacterial biofilm occurred. FIG. 1 provides a summary of these data. As illustrated in FIG. 1, thermolysin was effective in reducing the bacterial biofilm at concentrations of 0.00001 mg/mL-10 mg/mL, and was far more effective at reducing the bacterial biofilm than collagenase at these concentrations. The surprising nature of this discovery is based on the general knowledge that proteases are not thought to be overly effective on their own in reducing or eliminating bacterial biofilms.

The invention claimed is:

1. A method of treating a wound, mucous membrane lesion, or skin lesion infected or contaminated with a bacterial biofilm, the method comprising topically administering to the wound, mucous membrane lesion, or skin lesion a composition consisting essentially of thermolysin and a pharmaceutically acceptable carrier, wherein the bacterial biofilm is reduced or eliminated, and wherein the wound, mucous membrane lesion, or skin lesion does not include necrotic tissue and is not in need of debridement, wherein thermolysin is the only active ingredient in the composition that reduces or eliminates the biofilm.

2. The method of claim 1, wherein the bacterial biofilm is a gram-positive bacterial biofilm.

3. The method of claim 1, wherein the bacterial biofilm is a gram-negative bacterial biofilm.

4. The method of claim 1, wherein the wound is a chronic wound, and wherein the chronic wound is a diabetic foot ulcer, a venous ulcer, an arterial ulcer, a decubitus ulcer, a stasis ulcer, a pressure ulcer, or a burn.

5. The method of claim 1, wherein the concentration of thermolysin is at an amount that results in a reduction or elimination of the bacterial biofilm on the wound, mucous membrane lesion, or skin lesion.

6. The method of claim 1, wherein the concentration of thermolysin is from 0.0001 mg/mL to 10 mg/mL.

7. A method of reducing or eliminating a bacterial biofilm on a biological surface, the method comprising administering to the biological surface a composition consisting essentially of thermolysin and a pharmaceutically acceptable carrier, wherein the biological surface does not include necrotic tissue and is not in need of debridement, wherein the thermolysin is the only active ingredient in the composition that reduces or eliminates the biofilm.

8. The method of claim 7, wherein the biological surface is a chronic wound, and wherein the chronic wound is a diabetic foot ulcer, a venous ulcer, an arterial ulcer, a decubitus ulcer, a stasis ulcer, a pressure ulcer, or a burn.

9. The method of claim 7, wherein the biological surface is a skin lesion, a mucous membrane lesion, an internal organ, a body cavity, an oral cavity, a bone tissue, a muscle tissue, a nerve tissue, an ocular tissue, a urinary tract tissue, a lung tissue, a trachea tissue, a sinus tissue, an ear tissue, a dental tissue, a gum tissue, a nasal tissue, a vascular tissue, a cardiac tissue, an epithelium tissue, an epithelial lesion, a vaginal tissue, or a peritoneal tissue.

10. The method of claim 8, wherein the concentration of the thermolysin is at an amount that results in a reduction or elimination of the bacterial biofilm on the biological surface.

11. The method of claim 7, wherein the concentration of thermolysin is from 0.0001 mg/mL to 10 mg/mL.

12. The method of claim 1, wherein the pharmaceutically acceptable carrier comprises a lotion, solution, suspension, liquid, emulsion, cream, gel, hydrogel, ointment, paste, aerosol spray, aerosol foam, non-aerosol spray, non-aerosol foam, film, powder, or sheet.

13. A method of treating a wound, mucous membrane lesion, or skin lesion infected or contaminated with a bacterial biofilm, the method comprising topically administering to the wound, mucous membrane lesion, or skin lesion a composition consisting of thermolysin and a pharmaceutically acceptable carrier, wherein the bacterial biofilm is reduced or eliminated, and wherein the wound, mucous membrane lesion, or skin lesion does not include necrotic tissue and is not in need of debridement, wherein thermolysin is the only active ingredient in the composition that reduces or eliminates the biofilm.

14. The method of claim 7, wherein the pharmaceutically acceptable carrier comprises a lotion, solution, suspension, liquid, emulsion, cream, gel, hydrogel, ointment, paste, aerosol spray, aerosol foam, non-aerosol spray, non-aerosol foam, film, powder, or sheet.

15. A method of reducing or eliminating a bacterial biofilm on a biological surface, the method comprising administering to the biological surface a composition consisting of thermolysin and a pharmaceutically acceptable carrier, wherein the biological surface does not include necrotic tissue and is not in need of debridement, wherein the thermolysin is the only active ingredient in the composition that reduces or eliminates the biofilm.

* * * * *